United States Patent [19]

Houminer et al.

[11] 4,312,368
[45] Jan. 26, 1982

[54] SMOKING COMPOSITIONS

[75] Inventors: Yoram Houminer, Richmond; Harvey J. Grubbs, Mechanicsville, both of Va.

[73] Assignee: Philip Morris, Incorporated, New York, N.Y.

[21] Appl. No.: 122,901

[22] Filed: Feb. 20, 1980

[51] Int. Cl.³ .......................... A24B 3/12; A24B 3/36; A24B 3/38; A24B 3/40
[52] U.S. Cl. ................................ 131/277; 131/278; 131/279; 252/522 A
[58] Field of Search ............ 131/17 R, 144, 275–279; 252/522 A

[56] References Cited

U.S. PATENT DOCUMENTS

| | | | |
|---|---|---|---|
| 3,182,391 | 1/1974 | Means et al. | 131/17 R |
| 3,381,691 | 5/1968 | Schumacher et al. | 131/17 R |
| 3,402,051 | 9/1968 | Roberts | 99/140 |
| 3,625,224 | 12/1971 | Leffingwell | 131/17 R |
| 3,684,809 | 8/1972 | Mookherjee et al. | 131/144 |
| 3,705,158 | 12/1972 | Pittet et al. | 131/144 |
| 3,754,934 | 8/1973 | Pittet et al. | 131/144 |
| 3,764,349 | 10/1973 | Mookherjee et al. | 131/144 |
| 3,767,426 | 10/1973 | Evers et al. | 131/144 |
| 3,854,485 | 12/1974 | Mold et al. | 131/17 R |
| 3,881,025 | 4/1975 | Flament | 131/144 |
| 3,914,227 | 10/1975 | Pittet et al. | 131/144 |
| 4,036,237 | 7/1977 | Teng | 131/17 R |
| 4,141,906 | 2/1979 | Teng | 131/144 |
| 4,166,869 | 3/1980 | Flament et al. | 426/537 |

FOREIGN PATENT DOCUMENTS 1244068 8/1971 United Kingdom ............ 131/17 R

OTHER PUBLICATIONS

A. Bagget et al., *J Chromatography*, 97, 79 (1974).

*Primary Examiner*—V. Millin
*Attorney, Agent, or Firm*—Arthur I. Palmer, Jr.; George E. Inskeep

[57] ABSTRACT

This invention provides tobacco and non-tobacco smoking compositions which contain a heterocyclic-hydroxy-substituted carboxylate compound as a flavorant additive.

In one of its embodiments, this invention provides tobacco compositions which contain a heterocyclic-hydroxy-substituted alkanoate flavorant additive such as ethyl 2-(2-butyl)-3-hydroxy-3-methyl-3-(3-pyridyl)-propionate:

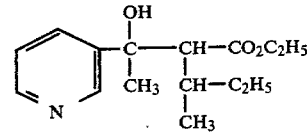

Under smoking conditions the above illustrated heterocyclic-hydroxy-substituted alkanoate additive and its pyrolysis products flavor the mainstream and sidestream smoke.

5 Claims, No Drawings

SMOKING COMPOSITIONS

BACKGROUND OF THE INVENTION

There has been continuing interest in organic materials which can function as flavoring agents for modifying or improving the flavor and aroma of tobaccos, foodstuffs, beverages and other such consumer products.

It has been established that alkylpyrazines are natural components of tobacco smoke, and that they most probably are important contributors to tobacco smoke flavor [A. Baggett et al, *J. Chromatog,* 97, 79 (1974)]. Further, it has been disclosed in the patent literature that addition of alkylpyrazines to tobacco results in an improvement in the flavor of smoking compositions as perceived by a test panel.

British Pat. No. 1,244,068 describes a method for influencing the smoke flavor of tobacco or a tobacco mixture which consists of treating the tobacco with a pyrazine derivative of the following chemical structure:

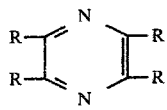

in which each R is independently a hydrogen atom, an aliphatic radical, an alicyclic radical or an aromatic hydrocarbon radical, such radicals having up to 9 carbon atoms, or R is a heterocyclic radical containing 4 to 9 carbon atoms.

U.S. Pat. No. 3,402,051 describes a process for imparting a popcorn-like flavor and aroma to tobacco and foodstuffs by the incorporation of a 2-acetylpyrazine derivative therein.

Other patents which disclose the addition of various pyrazine compounds to tobacco and foodstuffs as a means of providing flavor or flavor enhancement include U.S. Pat. Nos. 3,684,809; 3,705,158; 3,754,934; 3,764,349; 3,767,426; and 3,881,025.

U.S. Pat. No. 3,914,227 discloses pyridyl and pyrazyl ketones and their use in altering the organoleptic properties of tobacco and foodstuffs, and U.S. Pat. No. 4,166,869 discloses acylpyrimidines useful as flavorants for the same type of applications.

Alkylpyridines have also been found to be useful tobacco additives. As an example, U.S. Pat. No. 3,625,224 describes the use of methylpyridines, ethylpyridines and various dialkylpyridines as tobacco additives. U.S. Pat. No. 3,381,691 discloses 2-methyl-5-isopropylpyridine as a tobacco additive.

It is characteristic of pyridine, pyrazine, pyrimidine and other heterocyclic derivatives employed as tobacco flavorants in the prior art, as illustrated by the above described technical literature, that the respective heterocyclic derivatives have the disadvantage of both high volatility and low odor threshold. Both of these properties significantly restrict the extent that these heterocyclic derivatives can be utilized as flavorants in tobacco compositions. A quantity of a pyrazine or pyridine derivative in a tobacco composition sufficient to have a noticeable effect in low delivery cigarettes causes a marked pack aroma.

In a similar manner, the incorporation in tobacco of flavorants in the form of clathrates has been found to be unsatisfactory, since the yield of flavor when tobacco containing such clathrates is burned is very low. Likewise, the yield of flavorant is low when an ester such as menthyl succinate or menthyl borate is incorporated into a tobacco composition that is subsequently burned.

When an aldehyde flavorant such as cinnamaldehyde is added to a smoking composition, the loss of the flavorant during the manufacturing process and during storage is high, due to the relatively high vapor pressure of the aldehydic compound.

Further, as described in U.S. Pat. No. 3,782,391 alkyl esters of beta-methyl valeric acid are known to impart a fruity, apple-like aroma and a nut-like flavor when incorporated in tobacco. However, as noted in U.S. Pat. No. 3,854,485, such flavorant compounds are relatively valuable substances with a low odor threshold, and they present an evaporation problem in prolonged storage of the flavored tobacco compositions. Other esters such as monoalkyl and dialkyl malonates are known to provide a tobacco smoke with a fermented apple-peel and walnut-like flavor and aroma, but such esters yield only a limited form of flavor enhancement in tobacco products.

U.S. Pat. No. 4,036,237 endeavors to overcome some of the disadvantages of the above-described flavorant technology. The said patent provides for the incorporation in smoking compositions of a flavorant compound which imparts cherry-like or fruity flavor to the smoke thereof, which flavorant compound is not lost during the manufacture and storage of the flavored smoking composition, and which is readily released when the smoking composition is burned. Illustrative of a U.S. Pat. No. 4,036,237 flavorant compound is ethyl 2,2-dimethyl-3-hydroxy-3-phenylpropionate.

There remains a need for smoking compositions with enhanced flavor and aroma that do not exhibit the various disadvantages of prior art smoking compositions which contain a relatively volatile compound as a flavorant additive.

Accordingly, it is a main object of this invention to provide tobacco and non-tobacco smoking compositions which have incorporated therein a flavorant additive which is characterized by low volatility and low pack aroma.

It is another object of this invention to provide smoking compositions of tobacco and non-tobacco materials, and blends thereof, containing a heterocyclic-hydroxy-substituted carboxylate flavorant additive, which smoking compositions are adapted to impart flavor and aroma to the mainstream and sidestream smoke under smoking conditions.

It is a further object of this invention to provide novel heterocyclic-hydroxy-substituted carboxylate compounds which can be subjected to pyrolysis conditions to release heterocyclic and carboxylic constituents which can enhance the flavor and aroma of smoking compositions and foodstuffs.

Other objects and advantages of the present invention shall become apparent from the accompanying description and examples.

DESCRIPTION OF THE INVENTION

One or more objects of the present invention are accomplished by the provision of a smoking composition which comprises an admixture of (1) combustible filler selected from natural tobacco, reconstituted tobacco and non-tobacco substitutes, and (2) between about 0.00001 and 2 weight percent, based on the total weight of filler, of a heterocyclic-hydroxy-substituted carboxylate compound corresponding to the formula:

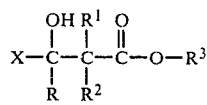

wherein X is a heterocyclic substituent containing between about 2–12 carbon atoms, and any heteroatom in X is selected from oxygen, nitrogen and sulfur; R is a substituent selected from aliphatic, alicyclic and aromatic groups containing between about 1–12 carbon atoms; $R^1$ and $R^2$ are hydrogen or substituents selected from aliphatic, alicyclic and aromatic groups containing between about 1–12 carbon atoms, and $R^1$ and $R^2$ when taken together with connecting elements form an alicyclic structure; and $R^3$ is a substituent selected from aliphatic alicyclic and aromatic groups containing between about 1–12 carbon atoms.

Illustrative of the heterocyclic X substituent in the formula represented above are furyl, tetrahydrofuryl, piperidyl, pyrrolidyl, indyl, pyrazolyl, imidazolyl, pyridyl, pyridazyl, pyrimidyl, pyrazyl, quinolyl, triazolyl, thienyl, tetrahydrothienyl, thiazyl, and the like, and the same type of heterocyclic structures which contain one or more alkyl groups of about 1–4 carbon atom content.

Preferred heterocyclic X substituents in the formula are those selected from pyrazyl and pyridyl radicals corresponding to the chemical structures:

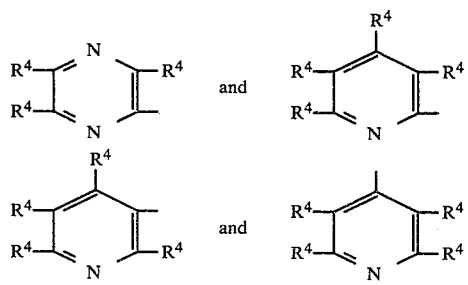

where $R^4$ is a substituent selected from hydrogen and $C_{1-4}$ lower alkyl groups.

Illustrative of the R, $R^1$, $R^2$ and $R^3$ substituents in the formula represented above are groups which include methyl, propenyl, butyl, pentyl, hexenyl, methoxyethyl, acetyl, cyclopropyl, cyclobutyl, cyclopentyl, cyclohexyl, menthyl, furyl, tetrahydrofuryl, piperidyl, pyrrolidyl, pyrazolyl, phenyl, tolyl, xylyl, benzyl, phenylethyl, methoxyphenyl, naphthyl, pyridyl, pyridazyl, pyrimidyl, pyrazyl, and the like.

As noted previously, $R^1$ and $R^2$ additionally can be hydrogen, and when taken together with the connecting elements form an alicyclic group such as cyclopentyl, cyclohexyl, cycloheptyl, menthyl, and the like.

A heterocyclic-hydroxy-substituted carboxylate compound corresponding to the formula represented above is a low volatility flavorant which under normal smoking conditions, or other comparably intensive localized heating conditions, volatilizes and evolves as a gaseous component. Concomitantly, a portion of the heterocyclic-hydroxy-substituted carboxylate compound pyrolyzes into products which respectively also exhibit flavorant properties. These secondary flavorant compounds are released in accordance with the following illustrated reaction mechanism:

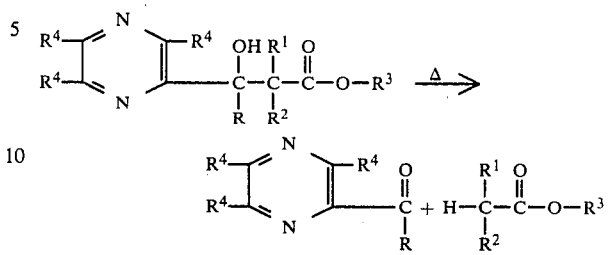

Each of the pyrolysis products illustrated above can impart flavor and aroma to tobacco and non-tobacco smoke under smoking conditions.

PREPARATION OF HETEROCYCLIC-HYDROXY-SUBSTITUTED CARBOXYLATE COMPOUNDS

One method of preparing the heterocyclic-hydroxy-substituted carboxylate compounds of the present invention is by the reaction of an alkanoate derivative with a carbonyl derivative, both of which derivatives are appropriately substituted in a manner as previously defined:

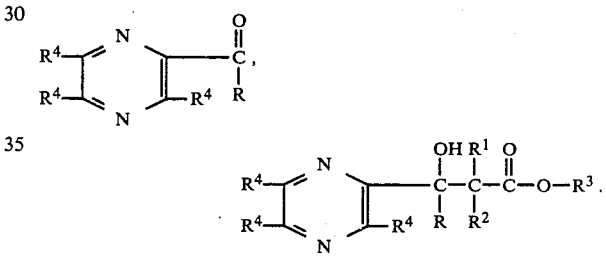

The reaction is conducted in the presence of a strong base such as lithium diisopropylamide, or alkali metal hydride. The strong base initiates the in situ formation of an anion intermediate:

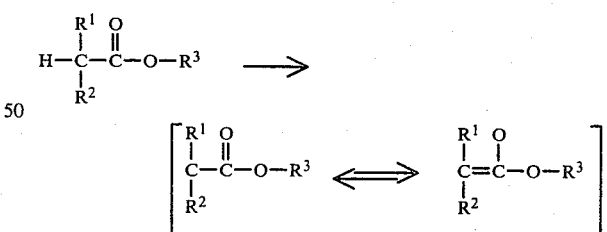

Preferably, the base is added to the alkanoate starting material in an inert solvent medium maintained at a temperature between about −80° and 50° C. and under an inert atmosphere. This procedure is followed by the addition of the heterocyclic-carbonyl compound to the reaction medium at a temperature between about −80° and 25° C.

Another method of preparing the heterocyclic-hydroxy-substituted carboxylate compounds of the present invention is by means of a Reformatsky-type reaction [R. L. Shriver, *Organic Reactions*, Vol. I, pp 1–37. John Wiley & Sons, Inc., New York (1942)], which may be generalized as follows with appropriately substituted starting materials:

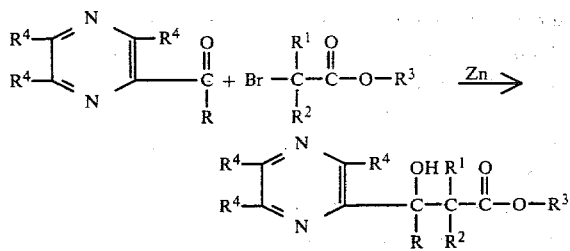

The first method of preparation described above has advantages over the Reformatsky method of preparation, since the first method does not require a costly bromine-containing ester co-reactant, and it permits a greater latitude in selection of the ester co-reactant.

The resultant heterocyclic-hydroxy-substituted carboxylate addition products obtained by either of the two preparative methods illustrated above are odorless, normally liquid compounds of high boiling point.

PREPARATION OF TOBACCO COMPOSITIONS

The present invention smoking compositions can be prepared by admixing natural tobacco and/or reconstituted tobacco and/or a non-tobacco substitute with between about 0.00001 and 2 weight percent based on the weight of the smoking composition, of a flavorant additive which corresponds to one of the structural formulae set forth hereinabove in definition of the heterocyclic-hydroxy-substituted carboxylate compounds.

The invention heterocyclic-hydroxy-substituted carboxylate flavorant additive can be incorporated into the tobacco in accordance with methods known and used in the art. Preferably the flavorant additive is dissolved in a solvent such as water, alcohol, or mixtures thereof, and then sprayed or injected into the tobacco or non-tobacco substitute matrix. Such method ensures an even distribution of the flavorant additive throughout the tobacco, and thereby facilitates the production of a more uniform smoking composition. Alternatively, the flavorant may be incorporated as part of a concentrated tobacco extract which is applied to a fibrous tobacco web as in the manufacture of reconstituted tobacco. Another suitable procedure is to incorporate the flavorant in tobacco or non-tobacco substitute filler in a concentration between about 0.5–5 weight percent, based on the weight of filler, and then subsequently to blend the treated filler with filler which does not contain flavorant additive.

The term "non-tobacco substitute" is meant to include smoking filler materials such as are disclosed in U.S. Pat. Nos. 3,529,602; 3,703,177; 3,796,222; 4,019,521; 4,079,742; and references cited therein; incorporated herein by reference.

Illustratively, U.S. Pat. No. 3,529,602 describes a burnable sheet which may be used as a tobacco substitute, which sheet contains ingredients which include (1) a film-forming ingredient comprising a pectinaceous material derived from tobacco plant parts and having an acid value in excess of 30 milligrams of potassium hydroxide per gram, and (2) a mineral ingredient comprising an alkali metal salt, an alkaline earth metal salt or a clay.

U.S. Pat. No. 3,703,177 describes a process for preparing a non-tobacco smoking product from sugar beet pulp, which process involves the acid hydrolysis of the beet pulp to release beet pectins, and at least an alkaline earth treatment thereafter to cause crosslinking of the pectins and the formations of a binding agent for the exhausted beet matrix.

U.S. Pat. No. 3,796,222 describes a smoking product derived from coffee bean hulls. The hulls are treated with reagents that attack the alkaline earth metal crosslinks causing the release of the coffee pectins. The pectins act as a binding agent and together with the treated hulls may be handled and used similarly to a tobacco product.

U.S. Pat. No. 4,019,521 discloses a process for forming a smoking material which involves heating a cellulosic or carbohydrate material at a temperature of 150°–750° C. in an inert atmosphere for a period of time sufficient to effect a weight loss of at least 60 percent but not more than 90 percent.

U.S. Pat. No. 4,079,742 discloses a process for the manufacture of a synthetic smoking product from a cellulosic material, which process involves a pyrolysis step and a basic extraction step to yield a resultant matrix which has a tobacco-like brown color and has improved smoking characteristics.

With respect to the quantity of heterocyclic-hydroxy-substituted carboxylate compound employed as a flavorant in the invention smoking compositions, it is to be noted that as little as 0.00001 percent, based on the total weight of filler, produces pyrolysis products which can be detected subjectively by an experienced smoking panel. This is a unique and unexpected aspect of the type of flavorant employed in the invention tobacco compositions, for the reason that comparative prior art tobacco flavorants are not known to exhibit this unusual degree of organoleptic potency. The high potency of an invention flavorant compound is advantageous since it permits the use of an exceptionally small quantity of the said flavorant in a smoking composition for the purpose of imparting flavor and aroma to the mainstream and sidestream smoke under smoking conditions. It is particularly noteworthy that the flavorant pyrolysis products can be detected subjectively by an experienced smoking panel, notwithstanding that the pyrolysis products are derived from a flavorant which is present in the smoking composition in a parts per million range which is difficult to detect by conventional analytical methods.

In another embodiment, the present invention also contemplates the incorporation of one of the heterocyclic-hydroxy-substituted carboxylate compounds described above into an article of manufacture which is burned under controlled conditions within the environment of a human habitat. In particular, the combustible articles contemplated are those such as candles, room deodorizers, manufactured fireplace fuel, and the like, the burning of which evolves a gaseous effluent which can be sensed by individuals within olfactory proximity. As it is apparent, wood logs can also be treated with a solution of a heterocyclic-hydroxy-substituted carboxylate compound prior to ignition in a fireplace.

The incorporation of between about 0.01 and 10 weight percent of a novel heterocyclic-hydroxy-substituted carboxylate compound of the present invention into a candle, for example, can introduce a pleasant aroma or fragrance into a confined living space when the candle is lighted.

In a further embodiment, the present invention provides a method for improving the flavor of a foodstuff (e.g., a meat-containing or meat-simulating product) which comprises contacting the foodstuff with a nontoxic gaseous effluent which is generated by the burning of a combustible material (e.g., a solid fuel) having admixed therewith between about 0.01 and 10 weight percent, based on the weight of combustible content, of a heterocyclic-hydroxy-substituted carboxylate compound of the present invention. Illustrative of one of the applications contemplated is the incorporation of the heterocyclic-hydroxy-substituted carboxylate compound in a smoke-house system for curing meats. Also, an invention substituted carboxylate compound can be incorporated in manufactured carbonaceous fuels (e.g., charcoal briquettes) which are used for broiling raw meat and fish products.

As it is apparent, a present invention heterocyclic-hydroxy-substituted carboxylate compound can be employed with optimal advantage in any application for adding flavor or enhancing the flavor of a foodstuff in which the foodstuff is subjected to a cooking cycle. The substituted carboxylate compound can be admixed with or applied to the surface of foodstuffs prior to or during the cooking phase. The substituted carboxylate compound can be blended with edible solids or liquids to facilitate its application as a flavorant additive. A blend of between about 0.01 and 10 weight percent of substituted carboxylate compound in vegetable oil, for example, is a convenient medium for imparting flavor to foodstuffs in deep-fry operations. The substituted heterocyclic compound can also be incorporated as a flavorant additive in prepared sauces, gravies and dressings. Suitable edible vehicles or carriers for a present invention substituted heterocyclic compound include fats and oils such as cottonseed oil, soy bean oil, olive oil, and peanut oil; emulsified fats and oils such as butter and margarine; gums such as guar, locust bean, gum arabic, carrageenen; and the like.

The following examples are further illustrative of the present invention. The reactants and other specific ingredients are presented as being typical, and various modifications can be derived in view of the foregoing disclosure within the scope of the invention.

EXAMPLE I

Preparation Of Ethyl 2-(2-Butyl)-3-hydroxy-3-methyl-3-(3-pyridyl)propionate

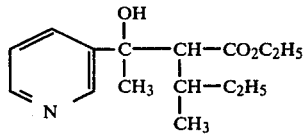

To a solution of diisopropylamine (22.2 grams, 0.22 mole) in 400 milliliters of anhydrous ether at 0° C., is added under nitrogen with stirring a solution of butyllithium in hexane (96 milliliters, 0.22 mole). The resulting mixture is stirred at 0° C. for 15 minutes, and then cooled to −78° C. A solution of ethyl β-methylvalerate (28.8 grams, 0.2 mole) in 80 milliliters of ether is added slowly over a period of 5 minutes. The mixture is stirred for 20 minutes at −78° C., at which time the formation of the enolate is completed.

To the above solution is added, with stirring, a solution of 3-acetylpyridine (24.2 grams, 0.2 mole) in 80 milliliters of ether. The mixture is stirred for 15 minutes at −78° C. and then allowed to warm up to room temperature (2 hours). Water is added and the ether layer is separated, washed with water, dried with magnesium sulfate and evaporated under reduced pressure to give an oil which weighs 48.0 grams. The oil is distilled in a Kugelrohr apparatus to yield 39.5 grams (74.5%) of the pure product, b.p. 95°–96° C. (air bath temperature) at 0.05 mm Hg.

Analysis calculated for $C_{15}H_{23}NO_3$: C,67.89; H,8.74; N,5.28. Found: C,67.62; H,8.82; N,5.21.

Employing the same procedure as described above, the following heterocyclic-hydroxy-substituted carboxylate compounds are prepared by the interaction of the appropriately substituted heterocyclic ketone reactant and ester reactant:

Phenyl 2-cyclohexyl-3-ethyl-3-hydroxy-3-(2-pyridyl)propionate;

4-Piperidyl 2-methyl-3-hydroxy-3-methyl-3-(2-tetrahydrothienyl)propionate;

Cyclopentyl 2,2-dimethyl-3-hydroxy-3-phenyl-3-(4-pyridyl)propionate;

Ethyl 2-(2-butyl)-3-hydroxy-3-methyl-3-(-2-pyrrolidyl)propionate;

EXAMPLE II

Preparation Of Ethyl 2-(2-Butyl)-3-hydroxy-3-methyl-3-(2-pyrazyl)propionate

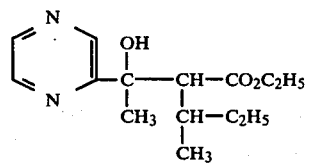

The reaction of 2-acetylpyrazine (12.2 grams, 0.1 mole) with the enolate of ethyl β-methylvalerate (14.4 grams, 0.1 mole), is carried out as described in Example I. Distillation gives 14.4 grams (54%) of the pure product, b.p. 80°–85° C. (air bath temperature) at 0.025 mm Hg.

Analysis calculated for $C_{14}H_{22}N_2O_3$: C,63.13; H,8.33; N,10.52. Found: C,62.99; H,8.41; N,10.69.

Employing the same procedure as described in Example I, the following heterocyclic-hydroxy-substituted carboxylate compounds are prepared by the interaction of the appropriately substituted heterocyclic ketone reactant and ester reactant:

Cyclohexen-3-yl-2,2-dimethyl-3-hydroxyl-3-(1-naphthyl)-3-(2,3-diethyl-5-pyrazyl)propionate;

2-pyrazyl 3-(2-butyl-3-pyrazyl)-3-hydroxy-3-phenyl-propionate;

Ethyl 2-(2-butyl)-3-hydroxy-3-methyl-3-(2-pyrimidyl)propionate;

3-Cyclohexenyl 2-methyl-3-hydroxy-3-methyl-3-(2-imidazolyl)propionate.

EXAMPLE III

Amyl 3-Hydroxy-3-methyl-3-(4-pyridyl)propionate

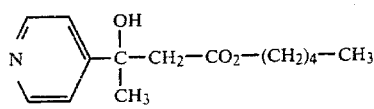

The reaction of 4-acetylpyridine (24.2 grams, 0.2 mole) with the enolate of amyl acetate (26.0 grams, 0.2 mole) is carried out as described in Example I. Distillation yields 37.2 grams (74%) of the pure product b.p. 102°–105° C. (air bath temperature) at 0.05 mm Hg.

Analysis calculated for $C_{14}H_{21}NO_3$: C,66.90; H,8.42; N,5.57. Found: C,66.93; H,8.59; N,5.53.

EXAMPLE IV

Pyrolysis of Ethyl 2-(2-Butyl)-3-hydroxy-3-methyl-3-(3-pyridyl)propionate

A 100 milligram quantity of the hydroxy ester described in Example I is pyrolyzed in a sealed tube at 250° C. for 5 minutes.

Analysis of the pyrolysis product mixture by gas chromatography and preparative thin layer chromatography indicates that the mixture consists of 12 milligrams of the hydroxy ester starting material, and 85 milligrams of a 1:1 mixture of 3-acetylpyridine and ethyl β-methylvalerate.

EXAMPLE V

Pyrolysis Of Ethyl 2-(2-Butyl-3-hydroxy-3-methyl-3-(2-pyrazyl) propionate

A 200 milligram quantity of the hydroxy ester described in Example II is pyrolyzed in a sealed tube at 250° C. for 5 minutes.

Analysis of the pyrolysis product mixture by gas chromatography and preparative thin layer chromatography indicates that the mixture consisted of 160 milligrams of the hydroxy ester starting material, and 40 milligrams of a 1:1 mixture of 2-acetylpyrazine and ethyl β-methylvalerate.

EXAMPLE VI

Pyrolysis Of Amyl 3-Hydroxy-3-methyl-3-(4-pyridyl)propionate

A 100 milligram quantity of the hydroxy ester described in Example III is pyrolyzed in a sealed tube at 400° C. for 3 minutes. Analysis of the pyrolysis mixture by gas chromatography indicates the presence of about 30% of a mixture in a 1:1 ratio of amyl acetate and 4-acetylpyridine. The remainder of the mixture contains unreacted starting material.

EXAMPLE VII

Preparation Of Smoking Compositions Containing A Flavorant Compound

Cigarettes are fabricated employing a blend of tobaccos treated with an ethanolic solution of ethyl 2-(2-Butyl)-3-hydroxy-3-methyl-3-(3-pyridyl)propionate to provide 0.00001% of the compound by weight of the tobacco. The cigarettes are targeted to deliver approximately 3 mg of tar per cigarette. Untreated controls are prepared using the identical tobacco blend, and the treated cigarettes are compared to the controls by an experienced smoking panel. The treated cigarettes are found to have a distinct fruity note, more body and more response as compared to the controls.

In the same manner, cigarettes are fabricated employing tobacco containing 0.00001% of ethyl 2-(2-Butyl)-3-hydroxy-3-methyl-3-(2-pyrazyl)propionate by weight of the tobacco. The cigarettes are targeted to deliver 3 mg tar per cigarette. Untreated controls are prepared using the identical tobacco, and the treated cigarettes are compared to the controls by an experienced smoking panel. The treated cigarettes are found to have a distinct fruity note, more body and more response as compared to the controls.

What is claimed is:

1. A smoking composition comprising an admixture of (1) combustible filler selected from natural tobacco, reconstituted tobacco and non-tobacco substitutes, and (2) between about 0.00001 and 2 weight percent, based on the total weight of filler, of a heterocyclic-hydroxy-substituted carboxylate compound corresponding to the formula:

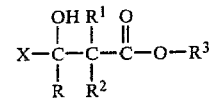

wherein X is a heterocyclic substituent containing between about 2–12 carbon atoms, and any heteroatom in X is selected from oxygen, nitrogen, and sulfur; R is a substituent selected from aliphatic, alicyclic and aromatic groups containing between about 1–12 carbon atoms; $R^1$ and $R^2$ are hydrogen or substituents selected from aliphatic, alicyclic and aromatic groups containing between about 1–12 carbon atoms, and $R^1$ and $R^2$ when taken together with connecting elements form an alicyclic structure; and $R^3$ is a substituent selected from aliphatic, alicyclic and aromatic groups containing between about 1–12 carbon atoms.

2. A smoking composition in accordance with claim 1 wherein the non-tobacco substitutes are selected from pectinaceous, cellulosic and carbohydrate materials.

3. A smoking composition in accordance with claim 1 wherein X is a heterocyclic substituent selected from pyrazyl and pyridyl radicals corresponding to the chemical structures:

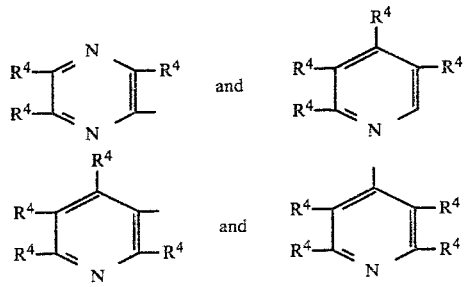

where $R^4$ is a group selected from hydrogen and lower alkyl groups.

4. A method of preparing a smoking composition which is adapted to impart flavoring to the mainstream and sidestream smoke under smoking conditions, which method comprises incorporating into natural tobacco, reconstituted tobacco or non-tobacco substitute between about 0.00001 and 2 weight percent, based on composition weight, of a flavorant additive corresponding to the formula:

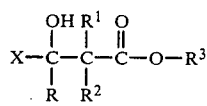

wherein X is a heterocyclic substituent containing between about 2-12 carbon atoms, and any heteroatom in X is selected from oxygen, nitrogen and sulfur; R is a substituent selected from aliphatic, alicyclic and aromatic groups containing between about 1-12 carbon atoms; $R^1$ and $R^2$ are hydrogen or substituents selected from aliphatic, alicyclic and aromatic groups containing between about 1-12 carbon atoms, and $R^1$ and $R^2$ when taken together with connecting elements form an alicyclic structure; and $R^3$ is a substituent selected from aliphatic, alicyclic and aromatic groups containing between about 1-12 carbon atoms.

5. A method of improving the aroma imparted by the burning of a combustible article of manufacture within the environment of a human habitat, which method comprises incorporating into said article of manufacture prior to its combustion between about 0.01 and 10 weight percent, based on the weight of combustible content, of a heterocyclic-hydroxy-substituted carboxylate compound corresponding to the formula:

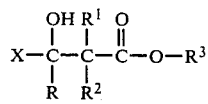

wherein X is a heterocyclic substituent containing between about 2-12 carbon atoms, and any heteroatom in X is selected from oxygen, nitrogen and sulfur; R is a substituent selected from aliphatic, alicyclic and aromatic groups containing between about 1-12 carbon atoms; $R^1$ and $R^2$ are hydrogen or substituents selected from aliphatic, alicyclic and aromatic groups containing between about 1-12 carbon atoms, and $R^1$ and $R^2$ when taken together with connecting elements form an alicyclic structure; and $R^3$ is a substituent selected from aliphatic, alicyclic and aromatic groups containing between about 1-12 carbon atoms.

* * * * *